(12) United States Patent
Romanenko et al.

(10) Patent No.: US 6,753,290 B1
(45) Date of Patent: Jun. 22, 2004

(54) CATALYTIC COMPOSITION, METHOD FOR MANUFACTURING THEREOF AND METHOD FOR THE PURIFICATION OF TEREPHTHALIC ACID

(75) Inventors: Anatoly Vladimirovich Romanenko, Novosibirsk (RU); Vladimir Alexandrovich Likholobov, Novosibirsk (RU); Maria Nikolaevna Timofeeva, Novosibirsk (RU); Jhung Sung Hva, Taejeon-Si (KR); Park Jun Seok, Taejeon-Si (KR)

(73) Assignees: Institut Kataliza Imeni G.K. Boreskova Sibirskogo Otdelenia Rossiiskoi Akademii Nauk, Lavrentieva (RU); Samsung General Chemicals Co., Ltd., Seoul (KR)

( * ) Notice: Subject to any disclaimer, the term of this patent is extended or adjusted under 35 U.S.C. 154(b) by 0 days.

(21) Appl. No.: 09/980,774

(22) PCT Filed: Dec. 9, 1999

(86) PCT No.: PCT/RU99/00477

§ 371 (c)(1),
(2), (4) Date: May 6, 2002

(87) PCT Pub. No.: WO01/08798

PCT Pub. Date: Feb. 8, 2001

(30) Foreign Application Priority Data

Jul. 29, 1999 (RU) .......................................... 99116348

(51) Int. Cl.$^7$ .......................... B01J 21/18; B01J 23/40; C07C 51/16; C07C 51/42
(52) U.S. Cl. ...................... 502/185; 502/182; 562/412; 562/485; 562/487
(58) Field of Search ............................... 502/182, 185; 562/412, 485, 487

(56) References Cited

U.S. PATENT DOCUMENTS

| | | | |
|---|---|---|---|
| 2,857,337 A | 10/1958 | Hamilton et al. | 252/472 |
| 3,138,560 A | 6/1964 | Keith et al. | 252/447 |
| 3,456,001 A | 7/1969 | Olsen | 260/525 |
| 4,201,872 A | 5/1980 | Kimura et al. | 562/487 |
| 4,394,299 A | 7/1983 | Puskas et al. | 252/447 |
| 4,415,479 A | 11/1983 | Puskas et al. | 502/85 |
| 4,421,676 A | 12/1983 | Puskas et al. | 502/185 |
| 4,467,110 A | * 8/1984 | Puskas et al. | 562/487 |
| 4,476,242 A | * 10/1984 | Puskas et al. | 502/185 |
| 4,629,715 A | 12/1986 | Schroeder | 502/185 |
| 4,728,630 A | 3/1988 | Schroeder et al. | 502/185 |
| 4,791,226 A | 12/1988 | Puskas et al. | 562/487 |
| 4,892,972 A | 1/1990 | Schroeder et al. | 562/487 |
| 5,723,659 A | * 3/1998 | White | 562/485 |

FOREIGN PATENT DOCUMENTS

| | | |
|---|---|---|
| EP | 0222499 | 5/1987 |
| EP | 0222500 | 5/1987 |
| GB | 994769 | 6/1965 |
| GB | 1578725 | 11/1980 |
| SU | 1660282 | 2/1997 |

OTHER PUBLICATIONS

Likholobov, V.A., et al. "New Carbon–Carbonaceous Composites for Catalysis and Adsorption" Sep. 1994 React. Kinet. Catal. Lett. vol. 54, No. 2, p. 381–411, (1995).

* cited by examiner

Primary Examiner—Mark L. Bell
Assistant Examiner—Patricia L. Hailey
(74) Attorney, Agent, or Firm—Ladas & Parry

(57) ABSTRACT

The present invention relates to catalyst compositions for purifying terephthalic acid from p-carboxybenzaldehyde, based on Group VIII metals, comprising crystallites of catalytically active palladium or of palladium and at least one metal of Group VIII of the Periodic Table of Elements, applied to the surface of a carbon material, wherein a mesoporous graphite-like material with the average mesopore size in the range of from 40 to 400 Å, the proportion of the mesopores in the total pore volume of at least 0.5, and the degree of graphite-similarity of at least 20% is used as the carbon material, in which metal crystallites are distributed in the volume of the carbon material granules in such a manner that the distribution peaks of these crystallites should be at a distance from the outer surface of the granule corresponding to 1–30% of its radius. The present invention also relates to a method for preparing catalyst compositions, and to a method of purifying terephthalic acid suitable for the subsequent synthesis of polyester polymers and copolymers used in the manufacture of textile fibers.

18 Claims, No Drawings

CATALYTIC COMPOSITION, METHOD FOR MANUFACTURING THEREOF AND METHOD FOR THE PURIFICATION OF TEREPHTHALIC ACID

BACKGROUND OF THE INVENTION

The present invention relates to catalyst compositions for purifying terephthalic acid, based on Group VIII metals, to methods for preparing thereof, and to a method of purifying terephthalic acid suitable for the subsequent synthesis of polyester polymers and copolymers used in the manufacture of textile fibers.

It is of importance that terephthalic acid which is used as a monomer in the manufacture of polymer fibers should have a high purity. The main controllable quality parameters of pure terephthalic acid are the content of p-carboxybenzaldehyde and colored impurities in it.

Purified terephthalic acid is derived from less pure, technical grade or "crude" terephthalic acid by hydrofining the latter (treating in the presence of hydrogen) over Group VIII metal catalysts. Crude terephthalic acid is dissolved in water at an elevated temperature, and the resulting solution is hydrogenated in a vibrated reactor or in a reactor with a stationary bed, preferably in the presence of Group VIII metal catalysts. The methods of purification, composition of the catalysts, and processes for preparing these catalysts are described in numerous patents.

DESCRIPTION OF THE RELATED ART

The activity and selectivity of catalysts for the hydrofining of terephthalic acid depend on a great number of factors, such as the content of Group VIII metal(s) in the catalyst, the type of support, the method of applying Group VIII metal(s) to the support, and also on the distribution of the metal or metals of Group VIII were applied to a support, and also on the distribution of said metal(s) over the granule of the carrier.

Known in the art is a method of hydrofining terephthalic acid [UK Patent No. 994769, 1965], wherein a palladium-on-active carbon catalyst composition displays high activity in the reaction of purifying terephthalic acid from p-carboxy-benzaldehyde impurities. As supports for palladium other compounds, such as $SiO_2$, $Al_2O_3$, were also investigated. It was found that carbon carriers were the best, because they, in contrast to oxide carriers, are not subject to rapid degradation in corrosive hot aqueous solutions of terephthalic acid.

The results of investigating the influence of the nature of carbon carriers are known. It has been shown that active carbons prepared from vegetable, animal or mineral sources, preferably from coconut active carbon, are suitable for the production of palladium catalysts for the hydrofining of terephthalic acid. It is desirable that the surface area of such active carbons should be at least 600 $m^2/g$, and the size of granules should correspond to 3–6 mm. In U.S. Pat. No. 4,728,630, 1988 an additional characteristic of such active carbon is introduced, namely, the pH value of its aqueous suspension. In SU Patent No. 1660282, 1997 a possibility is disclosed of using, as a suitable carrier, an active porous carbonaceous material modified with pyrocarbon. In U.S. Pat. Nos. 4,415,479, 1983; 4,421,676, 1983; and 4,791,226, 1988 it is indicated that for a more effective process of the hydrofining of terephthalic acid from p-carboxybenzaldehyde it is important to prepare catalysts with a definite size of the particles of applied palladium. The size of such particles must be not greater than 35 Å. The authors of U.S. Pat. Nos. 4,394,299, 1983 and 4,791,226, 1988 also point out a positive effect of such distribution of palladium particles in the granule of a carbon material, when they predominate on the outer surface of the granule.

In many patents it is pointed out that along with monometallic catalysts, the incorporation of Ni, Co, Cu, Fe, Mn, U, Cr, as well as Ir, Rh, Pt and Ru, into the catalyst composition may produce positive effect on the catalytic activity of palladium.

According to other group of patents [U.S. Pat. Nos. 4,629,715, 1986 and 4,892,972, 1990], the most effective action of bimetallic catalysts is attained, when the catalysts are arranged in a reactor in layers, for instance, Pd/C and Rh/C instead of one layer (Rh+Pd)/C. The authors of U.S. Pat. No. 4,892,972, 1990 even claim a method with the use of a layered catalyst bed, e.g., Ru/C+Rh/C+Pd/C.

Usually, catalysts comprising Group VIII metals, particularly palladium catalysts, are prepared by the adsorption of a palladium salt from solution to the carrier. In one of the processes [U.S. Pat. No. 2,857,337, 1967] such salt is treated with a water-soluble metal hydroxide or with a basic carbonate, this being followed by the reduction to metallic palladium with the help of such reducing agents as formaldehyde, glucose, glycerol, etc.

According to Keith et al. [U.S. Pat. No. 3,138,560, 1964], on addition of sodium tetrachloropalladoate or palladium chloride to many of carbon carriers, a large part of palladium immediately precipitates in the form of lustrous film of metallic palladium. Catalysts prepared by such a method usually have low activity. An opinion was voiced that palladium directly reduces to metal owing to free electrons or to the presence on the carbon surface of such functional groups as aldehydes. Palladium catalysts in the step preceding the reduction are predominantly prepared by fixing palladium in the form of an insoluble compound, so to avoid the problems of migration of palladium particles and growth of crystallites which may originate during the reduction of palladium from solution.

Though p-carboxybenzaldehyde is the most harmful impurity, which is crucial for the quality of the terephthalic acid used for the manufacture of plastics and sharply deteriorates the quality of the latter, p-toluic acid (p-TA) is also an undesirable impurity, which must be removed from the aqueous solution of terephthalic acid, obtained as a result of hydrofining. Though such removal can be achieved to a large extent owing to the greater solubility of p-toluic acid as compared to terephthalic acid, in water nevertheless substantial amounts of p-toluic acid are trapped within purified terephthalic acid crystals in the step of terephthalic acid crystallization from solution.

To avoid this disadvantage attendant to the separation of p-toluic acid, it has been proposed to decarbonylate p-carboxybenzaldehyde in aqueous solutions to benzoic acid in the presence of a palladium-on-carbon catalyst, since benzoic acid is more soluble in water than p-toluic acid [U.S. Pat. No. 3,456,001, 1969]. However, the foregoing decarbonylation of p-carboxybenzaldehyde to benzoic acid produces equimolar amounts of carbon monoxide, a well-known poison for the noble metals such as palladium [U.S. Pat. No. 4,201,872, 1980]. To minimize catalyst poisoning, in the aforementioned US Patent it is proposed to carry out the decarbonylation at relatively low process pressures so as to minimize dissolved carbon monoxide concentration in the liquid reaction medium. The process pressure also must be controlled within a closely defined pressure range. The generated carbon monoxide is purged from the reactor as a gas.

It is known [U.S. Pat. No. 4,892,972, 1990], that the use in the aforesaid purification of crude terephthalic acid of a catalyst system comprising a first layer of catalyst particles containing a metal of Group VIII of the Periodic Table of Elements supported on a carbon carrier and a second layer of palladium-on-carbon catalyst particles and the passage of the aqueous solution of crude terephthalic acid through the aforesaid first layer of rhodium-on-carbon catalyst particles and then through the second layer of palladium-on-carbon catalyst particles permits the amount of p-toluic acid produced during purification of crude terephthalic acid to be minimized. Such method of using the aforesaid catalyst system does not promote the hydrogenation of p-carboxybenzaldehyde to p-toluic acid but instead promotes the decarbonylation of p-carboxybenz-aldehyde to benzoic acid, which is more soluble than p-toluic acid in water and thus is more readily separable than p-toluic acid from terephthalic acid upon crystallization of the latter. This permits a feed solution having a relatively higher p-carboxybenzaldehyde content to be processed more economically.

The closest method of purification is described in GB Patent No. 1578725, 1980, wherein the authors propose to use catalysts comprising 2 or more metals such as Pt, Pd, Rh, Ru, Os, Ir, Fe, Ni, Co, Cr, Mn and U, in which one of the metals is Pd or Pt. In said catalysts metals are in the form of an alloy, a physical mixture, or are applied to an active carbon support (3 to 6 mm granules). Hydrofining is carried out by treating a terephthalic acid solution with hydrogen in the presence of said catalysts at elevated temperatures (280° C.) and a pressure (~100 atm.). The rate of hydrogenation in the presence of a bimetallic catalyst (0.4% Pd-0.1% Pt)/C per gram of the catalyst is 20% higher than with the use of 0.5% Pd/C.

So, crude terephthalic acid containing p-carboxybenz-aldehyde and other impurities can be purified by hydrogenation over conventionally prepared catalysts based on Group VIII metals applied to carbon.

BRIEF OF SUMMARY OF THE INVENTION

The present invention solves the problem of providing selective and stable catalysts and processes, wherein crude terephthalic acid with a high initial content of p-carboxybenz-aldehyde would be selectively hydrogenated and/or decarboxylated into benzoic acid with a low residual content of p-carboxybenz-aldehyde.

Said problem is solved in the following manner: by using in a method for the purification of terephthalic acid a catalyst composition comprising crystallites of catalytically active palladium or palladium and at least one metal of Group VIII of the Periodic Table of Elements, applied to the surface of a carbon material, wherein a mesoporous graphite-like material with the average mesopore size in the range of from 40 to 400 Å, the proportion of the mesopores in the total pore volume of at least 0.5, and the degree of graphite-similarity of at least 20% is used as the carbon material, in which metal crystallites are distributed in the volume of the carbon material granules in such a manner that the distribution peaks of these crystallites should be at a distance from the outer surface of the granule corresponding to 1–30% of its radius.

The catalyst composition comprises crystallites of palladium and rhodium or of palladium and ruthenium, or of palladium and platinum; the total content of the metals varies within the range of from 0.3 to 3.0 percent by weight, the weight ratio of palladium to other metals varies within the range of from 0.1 to 10.0

The problem is also solved by the provision of a method of preparing a catalyst composition for the purification of terephthalic acid by applying catalytically active palladium or palladium and at least one of Group VIII metals to the surface of granules of a carbon carrier, with said granules being in contact with an aqueous solution of palladium salts or palladium salts and at least one of Group VIII metals to produce a metal salt-porous carbon precursor, in which method the precursor is dried and treated with a reducing agent in an amount sufficient for reducing the superficial metal salts to metal crystallites, wherein a mesoporous graphite-like material with the average mesopore size in the range of from 40 to 400 Å, the proportion of the mesopores in the total pore volume of at least 0.5, and the degree of graphite-similarity of at least 20% is used as the carbon material to produce a monometallic or bimetallic catalyst.

Said catalyst composition is prepared with the use of one of the following metal precursors:

$H_2PdCl_4$ or $Pd(NO_3)_2$;

$H_2PdCl_4$ or $RuOCl_3$ or $RuNO(NO_3)_3$;

$Pd(NO_3)_2$ and $RuOHCl_3$ or $RuNO(NO_3)_3$.

For preparing said catalyst composition, nitrate solutions of palladium and/or ruthenium salts are prepared with concentration of free nitric acid from 37 to 170 g/l. Bimetallic catalysts are prepared by applying metal precursors simultaneously or in succession.

We have found that such catalyst can be prepared, if mono- or bimetallic particles of Group VIII metals are applied to the surface of carbon materials having an average pore size of 40 to 200 Å and a considerable (from 20 to 60%) degree of graphite similarity; said metallic particles being distributed within the volume of the carbon carrier in such a manner that their distribution peaks are at a distance from the outer surface of said granule, equivalent to 1–30% of its radius.

As the aforesaid carbon materials carriers may be used, prepared by the heat treatment of plastics, and also synthesized in accordance with a special technology from gaseous hydro-carbons (V. A. Likhoborov et al., React. Kin. Cat. Lett., vol. 54, 2 (1995) 381–411), namely, Sibunit, KVU and various compos-ites based thereon. The physicochemical characteristics of some carbons are presented in Table 1. The tabulated data indicate that the aforesaid carbon materials in the set of such parameters as $V_{meso}/V_\Sigma$ and K sharply differ from conventional active carbons usually employed for producing catalysts for the hydrofining of terephthalic acid, prepared from vegetable, animal or mineral sources, preferably coconut active carbons tat are used for preparing conventional terephthalic acid hydrofining catalysts.

We have also found that if in the pores of such carbon materials the distribution of metal particles over the volume of the carrier granule is effected in such a manner that the distribution peak(s) will be found at as distance from the outer surface of the granule corresponding to 1–30% of its radius, then such catalyst has an enhanced service life on reuse. This effect is particularly manifest, when palladium and ruthenium are used as Group VIII metals. Furthermore, the presence of both palladium and ruthenium in the catalyst leads to the effect of synergism, rather than additive growth of the catalyst activity, especially if the distribution peaks of the particles of these metals are in the area adjacent to the outer surface of the catalyst granules.

We have also found that with such distribution of palladium and ruthenium particles in the granule of the mesoporous carbon material it is possible to replace a part of palladium by ruthenium, this leading not only to lower costs of the catalyst (since ruthenium is substantially cheaper than palladium), but also to a change in the ratio of concentrations of p-toluic and benzoic acids, which are the products of p-carboxybenzaldehyde conversion, towards the latter, this promoting the attaining of a higher quality of the obtained crystalline terephthalic acid.

For preparing the aforementioned catalysts, i.e., the catalysts containing mono- or bimetallic particles of palladium and ruthenium, applied to the surface of carbon carriers, it is possible to use such methods well-known in the literature as impregnating the carrier with solutions of various salts of palladium and ruthenium. However, as has been found, the best catalysts are obtained by using a method of spray-depositing acid solution of palladium and ruthenium salts on a suitable carbon carrier with subsequent treatment of the thus applied metal precursors with hydrogen.

Examples 1–35 presented hereinbelow characterize the catalysis compositions and methods of preparing them. Examples 7, 30–34 are given for comparison, and Examples 8 and 35 are given as a prototype. Examples 36–39 describe the employed methods of purifying terephthalic acid. Analytical results concerning the character of distribution of metallic particles inside the granule of the carrier and the quality of terephthalic acid purified with the use of the proposed compositions are presented in Tables 2–6.

EXAMPLE 1

A cylindrical rotated reactor is charged with 50 g of carbon carrier Sibunit 1 (the data on its physicochemical and texture properties are presented in Table 1). Here and in the Examples that follow the carrier is preliminarily purified from dust by boiling in distilled water. Then the carrier is discharged onto a sieve with 1 mm meshes and dried at 120° C. to constant weight. Aqueous solutions of $Na_2CO_3$ (0.364 mole/l; 13 ml) and $H_2PdCl_4$ (0.182 mole/l: 13 ml) with the same space velocity (2.5 ml/min) in the molar ratio $Na_2CO_3:H_2PdCl_4=2:1$ are fed to a nozzle, and the resulting mixture is sprayed into the reactor. The catalyst is discharged and dried under vacuum at 75° C. to constant weight. The subsequent operation of reducing is carried out in a tubular reactor it a flow of hydrogen at the temperature of 250° C. for 2 hours. Then the temperature is lowered from 250° C. to 40° C., at 110° C. hydrogen being displaced by nitrogen. The catalyst is washed with distilled water till the absence of the reaction with $AgNO_3$ for chlorine ions in the washwater, and dried under vacuum at 75° C. to constant weight. The procedure yields a Pd/Sib.1 catalyst with palladium content of 0.5 percent by weight. The electron probe microanalysis of the catalyst granules is carried out by scanning the granule section along the diameter on a MAR-3 micoanalyzer with a 1–2 $\mu$m diameter probe with accelerating voltage of 20 kV and current of 20–30 nA. As the characteristic of the active component distribution over the catalyst grain parameter $\Delta$ is used, which characterizes the thickness of the active metal layer in $\mu$m at ½ of the peak height.

The data on the distribution of palladium and ruthenium particles in the catalysts prepared in accordance with the Examples given in the present specification are listed in Table 2.

EXAMPLE 2

The catalyst is prepared as in Example 1, but instead of an aqueous solution of $H_2PdCl_4$, $RuOHCl_3$ is used (0.191 mole/l, 13 ml), and the concentration of the $Na_2CO_3$ solution (13 ml) corresponds to 0.382 mole/l; $Na_2CO_3:RuOHCL_2=2:1$. The procedure gives a Ru/Sib.1 catalyst with ruthenium content of 0.5 percent by weight.

EXAMPLE 3

The catalyst is prepared by combined application of Ru and Pd, using aqueous solutions of $RuOHCl_3$ and $H_2PdCl_4$ as metal precursors, respectively. For this purpose, a cylindrical rotated reactor is charged with 50 g of Sibunit 1 carbon carrier. 13 ml of an aqueous solution of $Na_2CO_3$ (0.371 mole/l) and 13 ml of $H_2PdCl_4$ (0.109 mole/l)+ $RuOHCl_3$ (0.076 mole/l) are fed to a nozzle with the same space velocity (2.5 ml/min) in the molar ratio $Na_2CO_3$: $(Ru+Pd)=2:1$, and the resulting mixture is sprayed into the reactor. The catalyst is discharged and dried under vacuum at 70° C. to constant weight. The subsequent operations of reducing, washing and drying are similar to Example 1. The resulting product is a (Ru–Pd)/Sib.1 catalyst containing 0.2 percent by weight of ruthenium and 0.3 percent by weight of palladium.

EXAMPLE 4

A cylindrical rotated reactor is charged with 50 g of Sibunit 1 carbon carrier. 26 ml of nitric aqueous solution of $Pd(NO_3)_2$ (0.091 mole/l) with the concentration of free $HNO_3$ equal to 170 g/l are fed to a nozzle and the resulting mixture is sprayed with the velocity of 5 ml/min into the reactor. The sample is placed into a tubular reactor and dried in a flow of air for 1 hour, while raising the temperature to 120° C., and then kept at this temperature for another 2 hours. Then the air is replaced by nitrogen and the temperature is raised to 250° C. (at this temperature decomposition of $Pd(NO_3)_2$ to palladium oxide occurs). Under these conditions the sample is kept for 3 hours and then cooled down to 150° C. Then nitrogen is replaced at this temperature by hydrogen, and the catalyst is reduced for 1 hour at 150° C., followed by raising the temperature to 250° C. and keeping the sample at this temperature for 2 hours. Then the temperature is lowered from 250° C. to 40° C., at 110° C. hydrogen being displaced by nitrogen. The resulting product is a Pd/Sib.1 catalyst containing 0.5 percent by weight of palladium. The catalyst thus prepared is used in Examples 24, 25 in the synthesis of bimetallic catalysts.

EXAMPLE 5

The catalyst is prepared as in Example 4, but instead of the aqueous nitric acid solution of $Pd(NO_3)_2$ 26 ml of an aqueous nitric acid solution of $RuNO(NO_3)_3$[1] (0.091 mole/l) with the concentration of free $HNO_3$ equal to 170 g/l. The resulting product is a Ru/Sib.1 catalyst containing 0.5 percent by weight of ruthenium.

[1] $RuNO(NO_3)_3$ is prepared by evaporating aqueous $RuOHCl_3$ to a syrupy state, dissolving the residue in concentrated $HNO_3$, and subsequently evaporating the solution to the syrupy state. Then concentrated $NHO_3$ is added, and the evaporation is carried out again. The residue is dissolved in water to the required concentration of Ru.

EXAMPLE 6

The catalyst is prepared by combined application of Ru and Pd, using aqueous nitric acid solutions of $RuNO(NO_3)_3$ and $Pd(NO_3)_2$ as metal precursors, respectively. For this purpose, a cylindrical rotated reactor is charged with 50 g of Sibunit 1 carbon carrier. 26 ml of an aqueous nitric acid solution of $RuNO(NO_3)_3$ (0.038 mole/l)+$Pd(NO_3)_2$ (0.054 mole/l) with the concentration of free $HNO_3$ equal to 170 g/l are fed to a nozzle and sprayed with the velocity of 5 ml/min into the reactor. Subsequent operations of drying, calcining and reducing are similar to those used in Example 4. The resulting product is a (Ru–Pd)/Sib.1 catalyst containing 0.2 percent by weight of ruthenium and 0.3 percent by weight of palladium.

EXAMPLE 7 (COMPARATIVE)

The catalyst is prepared as in Example 4, but instead of the Sibunit 1 carbon carrier CG-5 coconut carbon is used. The resulting product is a Pd/CG-5 catalyst containing 0.5 percent by weight of palladium.

EXAMPLE 8 (PROTOTYPE)

The catalyst is prepared as in Example 3, but instead of the Sibunit 1 carbon carrier CG-5 coconut carbon is used. The resulting product is a (Ru–Pd)/CG-5 catalyst containing 0.2 percent by weight of ruthenium and 0.3 percent by weight of palladium.

EXAMPLE 9

The catalyst is prepared as in Example 3, but 13 ml of an aqueous solution of $Na_2CO_3$ (0.366 mole/l) and 13 ml of $H_2PdCl_4$ (0.145 mole/l)+$RuOCl_3$ (0.038 mole/l) are fed to the nozzle; $Na_2CO_3$:(Ru+Pd)=2:1. The resulting product is a (Ru–Pd)/Sib.1 catalyst containing 0.1 percent by weight of ruthenium and 0.4 percent by weight of palladium.

EXAMPLE 10

The catalyst is prepared as in Example 3, but 13 ml of an aqueous solution of $Na_2CO_3$ (0.073 mole/l)+$RuOCl_3$ (0.115 mole/l) are fed to the nozzle; $Na_2CO_3$: (Ru+Pd)=2:1. The resulting product is a (Ru–Pd)/Sib.1 catalyst containing 0.3 percent by weight of ruthenium and 0.2 percent by weight of palladium.

EXAMPLE 11

The catalyst is prepared as in Example 6, but 26 ml of an aqueous nitric acid solution of $RuNO(NO_3)_3$ (0.019 mole/l)+$Pd(NO_3)_2$ (0.073 mole/l) with the concentration of free $HNO_3$ equal to 170 g/l are fed to the nozzle. The resulting product is a (Ru–Pd)/Sib.1 catalyst containing 0.1 percent by weight of ruthenium and 0.4 percent by weight of palladium.

EXAMPLE 12

The catalyst is prepared as in Example 6, but 26 ml of an aqueous nitric acid solution of $RuNO(NO_3)_3$ (0.057 mole/l)+$Pd(NO_3)_2$ (0.036 mole/l) with the concentration of free $HNO_3$ equal to 170 g/l are fed to the nozzle. The resulting product is a (Ru–Pd)/Sib.1 catalyst containing 0.3 percent by weight of ruthenium and 0.2 percent by weight of palladium.

EXAMPLE 13

The catalyst is prepared as in Example 5, but using 26 ml of an aqueous nitric acid solution of $RuNO(NO_3)_3$ (0.038 mole/l) with the concentration of free $HNO_3$ equal to 53 g/l. The resulting product is Ru/Sib.1 catalyst containing 0.2 percent by weight of ruthenium. The catalyst thus prepared is used in Example 18 in the synthesis of bimetallic catalysts.

EXAMPLE 14

The catalyst is prepared as in Example 13, but using 26 ml of an aqueous nitric acid solution of $RUNO(NO_3)_3$ (0.038 mole/l) with the concentration of free $HNO_3$ equal to 170 g/l. The resulting product is Ru/Sib.1 catalyst containing 0.2 percent by weight of ruthenium. The catalyst thus prepared is used in Example 19 in the synthesis of bimetallic catalysts.

EXAMPLE 15

The catalyst is prepared as in Example 4, but using 26 ml of an aqueous nitric acid solution of $Pd(NO_3)_2$ (0.054 mole/l) with the concentration of free $HNO_3$ equal to 53 g/l. The resulting product is a Pd/Sib.1 catalyst containing 0.3 percent by weight of palladium. The catalyst thus prepared is used in Examples 20, 22 in the synthesis of bimetallic catalysts.

EXAMPLE 16

The catalyst is prepared as in Example 15, but using 26 ml of an aqueous nitric acid solution of $Pd(NO_3)_2$ (0.054 mole/l) with the concentration of free $HNO_3$ equal to 170 g/l. The resulting product is a Pd/Sib.1 catalyst containing 0.3 percent by weight of palladium. The catalyst thus prepared is used in Example 21 in the synthesis of bimetallic catalysts.

EXAMPLE 17

The catalyst is prepared as in Example 1, but with feeding to the nozzle with the same space velocity (2.5 ml/min) in the molar ratio $Na_2CO_3$:$H_2PdCl_4$=2:1 aqueous solutions of $Na_2CO_3$ (0.218 mole/l; 13 ml) and $H_2PdCl_4$ (0.109 mole/l; 13 ml). The resulting product is a Pd/Sib.1 catalyst containing 0.3 percent by weight of palladium. The catalyst thus prepared is used in Example 23 in the synthesis of bimetallic catalysts.

EXAMPLE 18

The catalyst is prepared as in Example 17, but using Ru/Sib.1 from Example 13 instead of Sibunit 1. The resulting product is a Pd/Ru/Sib.1 catalyst containing 0.2 percent by weight of ruthenium and 0.3 percent by weight of palladium.

EXAMPLE 19

The catalyst is prepared as in Example 15, but using Ru/Sib.1 from Example 14 instead of Sibunit 1. The resulting product is a Pd/Ru/Sib.1 catalyst containing 0.2 percent by weight of ruthenium and 0.3 percent by weight of palladium.

EXAMPLE 20

The catalyst is prepared as in Example 2, but with feeding to the nozzle with the same space velocity (2.5 ml/min) in the molar ratio $Na_2CO_3$:$RuOHCl_3$=2:1 aqueous solutions of $Na_2CO_3$ (0.152 mole/l; 13 ml) and $RuOHCl_3$ (0.076 mole/l; 13 ml) and using Pd/Sib.1 from Example 15 instead of Sibunit 1. The resulting product is a Ru/Pd/Sib.1 catalyst containing 0.2 percent by weight ruthenium and 0.3 percent by weight of palladium.

EXAMPLE 21

The catalyst is prepared as in Example 13, but using Pd/Sib.1 from Example 16 instead of Sibunit 1. The resulting product is a Ru/Pd/Sib.1 catalyst containing 0.2 percent by weight of ruthenium and 0.3 percent by weight of palladium.

EXAMPLE 22

The catalyst is prepared as in Example 14, but using Pd/Sib.1 from Example 15 instead of Sibunit 1. The resulting product is a Ru/Pd/Sib.1 catalyst containing 0.2 percent by weight of ruthenium and 0.3 percent by weight of palladium.

EXAMPLE 23

The catalyst is prepared as in Example 13, but using Pd/Sib.1 from Example 17 instead of Sibunit 1. The resulting product is a Ru/Pd/Sib.1 catalyst containing 0.2 percent by weight of ruthenium and 0.3 percent by weight of palladium.

EXAMPLE 24

A cylindrical rotated reactor is charged with 50 g of Pd/Sib.1 prepared as described in Example 4. An aqueous solution of $H_2PtCl_6$ (0.00999 mole/l; 26 ml) is fed to the nozzle and sprayed with the velocity of 5 ml/min into the reactor. The subsequent operations of reducing, washing and drying are similar to those in Example 1. The resulting product is a Pt/Pd/Sib.1 catalyst containing 0.1 percent by weight of platinum and 0.5 percent by weight of palladium.

EXAMPLE 25

The catalyst is prepared as in Example 24, but using an aqueous solution of $RhCl_3$ (0.019 mole/l; 26 ml) instead of $H_2PtCl_6$. The resulting product is a Rh/Pd/Sib.1 catalyst containing 0.1 percent by weight of rhodium and 0.5 percent by weight of palladium.

EXAMPLES 26–27.

Catalysts are prepared in Example 4, but the concentration of free $HNO_3$ is 37 g/l (Example 26) and 147 g/l (Example 27). The resulting products are Pd/Sib.1 catalysts containing 0.5 percent by weight of palladium.

EXAMPLE 28

The catalyst is prepared as in Example 1, but with feeding to the nozzle 13 ml of an aqueous solution of $Na_2CO_3$ (0.727 mole/l) and 13 ml of $H_2PdCl_4$ (0.363 mole/l); $Na_2CO_3$:Pd= 2.1. The resulting product is a Pd/Sib.1 catalyst containing 1.0 percent by weight of palladium.

EXAMPLE 29

The catalyst is prepared as in Example 1, but with feeding to the nozzle 13 ml of an aqueous solution of $Na_2CO_3$ (1.453 mole/l) and 13 ml of $H_2PdCl_4$ (0.727 mole/l); $Na_2CO_3$:Pd= 2.1. The resulting product is a Pd/Sib.1 catalyst containing 2.0 percent by weight of palladium.

EXAMPLE 30 (COMPARATIVE)

The catalyst is prepared as in Example 4, but using AR-B active carbon instead of Sibunit 1 carbon carrier. The resulting product is a Pd/AR-B catalyst containing 0.5 percent by weight of palladium.

EXAMPLE 31 (COMPARATIVE)

The catalyst is prepared as in Example 4, but using L-2702 active carbon instead of Sibunit 1 carbon carrier. The resulting product is a Pd/L-2702 catalyst containing 0.5 percent by weight of palladium.

EXAMPLE 32 (COMPARATIVE)

The catalyst is prepared as in Example 4, but using FB-4 active carbon instead of Sibunit 1 carbon carrier. The resulting product is a Pd/FB-4 catalyst containing 0.5 percent by weight of palladium.

EXAMPLE 33 (COMPARATIVE)

The catalyst is prepared as in Example 1, but using KVU-1 carbon material instead of Sibunit 1 carbon carrier. The resulting product is a Pd/KVU-1 catalyst containing 0.5 percent by weight of palladium.

EXAMPLE 34 (COMPARATIVE)

The catalyst is prepared as in Example 1, but using CG-5 coconut carbon instead of Sibunit 1 carbon carrier. The resulting product is a Pd/CG-5 catalyst containing 0.5 percent by weight of palladium.

EXAMPLE 35 (PROTOTYPE)

The catalyst is prepared by combined application of Ru and Pd, using aqueous solutions of $H_2PtCl_6$ and $H_2PdCl_4$ as metal precursors, respectively. For this purpose, a cylindrical rotated reactor is charged with 50 g of CG-5 coconut carbon. 13 ml of an aqueous solution of $Na_2CO_3$ (0.330 mole/l) and 13 ml of $H_2PdCl_4$ (0.145 mole/l)+$H_2PtCl_6$ (0.020 mole/l) are fed to a nozzle with the same space velocity (2.5 ml/min) in the molar ratio $Na_2CO_3$:(Pt+Pd)= 2:1, and the resulting mixture is sprayed into the reactor. The catalyst is discharged and dried under vacuum at 70° C. to constant weight. The subsequent operations of reducing, washing and drying are similar to Example 1. The resulting product is a (Pt–Pd)/CG-5 catalyst containing 0.1 percent by weight of platinum and 0.4 percent by weight of palladium.

EXAMPLE 36

A stainless steel pot of a 457 Mini Parr Reactor is charged with 150 ml of distilled $H_2O$ and 12.9 g of impure terephthalic acid containing 8000 ppm of p-carboxybenzaldehyde and 126 ppm of p-toluic acid. The mixer rotor is modified in such a manner that it comprises a mesh basket adapted to receive catalyst granules. 0.170 g of granules of the catalyst prepared as described in Example 1 is placed on the bottom of the basket. The basket is secured on the rod of the mixer. Then an autoclave cover is placed onto the pot and screwed down tightly. The reactor is connected to the system. The system is purged with nitrogen, then with hydrogen, and the pressure is built up with hydrogen to 14 atm. The temperature on the control panel is set to be 250° C. and the furnace heating is switched on. As the temperature in the reactor reaches the preset value, a stirring device equipped with a magnetic drive (whose rotation speed is ~240 rpm) is switched on. The time when the stirring is started is recognized as the commencement of the experiment. The experiment lasts for 3 hours. The reaction mass is then cooled, and the setup is purged with nitrogen. After that the reactor is opened, the basket with the catalyst is disconnected from the rod of the mixer, and the catalyst is removed. The contents of the autoclave (a suspension of terephthalic acid in water) are transferred to a glass filter, washed with distilled water (50 ml) and dried under vacuum at 75° C. for 2 hours. From the resulting terephthalic acid powder samples are taken for impurity analysis.

The content of p-carboxybenzaldehyde in purified terephthalic acid is determined with the help of an OH-105 universal polarograph by voltammetric techniques in differential polariz-ation mode on a mercury-graphite electrode in accordance with an analytical signal with a maximum at the potential of −1.07 V, proportional to the concentration of p-carboxybenzaldehyde in terephthalic acid.

The concentration of p-toluic acid in purified terephthalic acid is determined by high-pressure liquid chromatography techniques on a Milichrom liquid chromatograph. A batch of terephthalic acid is dissolved in 0.3M $NH_4H_2PO_4$ and analyzed on a 2×80 mm column with anion-exchange resin Partisil, 10 SAX (Watman) as the stationary phase.

The color level (transparence) of purified terephthalic acid is determined by measuring directly the optical density of aqueous-alkaline solutions at 340 and 400 nm. For this purpose, 1.5 g of purified terephthalic acid is dissolved in 10 ml of 2M KOH solution. The solution is preliminarily centrifugated for 15 min with the rotation speed of 3000 rpm. The optical density is measured on a spectrophotometer (in our case on a Specord M40) in 10 mm-thick quartz cells against 2M KOH solution at 340 and 400 nm.

The analytic data on the quality of terephthalic acid purified by this method on the catalysts prepared in accordance with the Examples presented hereinabove are given in Table 3.

EXAMPLE 37

The method of purifying terephthalic acid is similar to that described in Example 35, the difference being in that 0.340 g of the catalyst is charged into the basket. The catalyst after the experiment (cycle) is washed directly in the basket with distilled water and used in the next cycle. The duration of testing one sample is from four to five cycles.

The analytic data on the quality of terephthalic acid purified by this method on the catalysts prepared in accordance with the Examples presented hereinabove are listed in Table 4.

EXAMPLE 38

The method of purifying terephthalic acid is similar to that described in Example 36, the difference being in that the purification is carried out on the catalysts prepared as described in Examples 3 and 34 with an increased initial content of p-carboxybenzaldehyde, equal to 30,000 ppm.

The analytic data on the quality of terephthalic acid purified by this method are presented in Table 5.

EXAMPLE 39

500 ml of distilled $H_2O$, 25 g of impure terephthalic acid containing 3552 ppm of 126 ppm of p-toluic acid are charged into a 750 ml stainless steel cylinder (solvent). After that the autoclave cover is put onto the cylinder and screwed down tightly. 2.0 g of the catalyst prepared as described in Example 1 are placed on a grid of a reactor comprising a stainless steel tube with an inner diameter of 10 mm, having a drain opening at the height of 110 mm from a lower grid, and fixed from the top with the second grid. The reactor is coupled to the solvent. The drain opening of the reactor via a thermostated steel capillary is tightly coupled to a crystallizer which comprises stainless steel autoclave having a capacity of 750 ml. The solvent, reactor and crystallizer are disposed in a heated temperature-controlled cabinet. The system is purged with nitrogen, then with hydrogen, $H_2$ being bubbled through the aqueous suspension of terephthalic acid in the solvent, and the pressure is brought up to 10 atm with hydrogen. On the control panel the temperature is set to be 250° C., and heating of the temperature-controlled cabinet is switched on. As soon as the temperature in the system reaches the prescribed value, hydrogen is supplied to the solvent with a constant space velocity by means of a gas flow regulator. Constant pressure in the system is maintained by keeping a pressure regulator disposed at the crystallizer outlet in "pulled back" position. As the gas gradually enters the system, it displaces the terephthalic acid solution from the solvent into the reactor, and the terephthalic acid solution is forced with a constant velocity through the catalyst bed from bottom upwards and drained through the drain opening into the crystallizer. Forcing the solution through the reactor takes 8 hours. The reaction mass is cooled down, and the setup is purged with nitrogen. The contents of the crystallizer (terephthalic acid suspension in water) are transferred to a glass filter, filtered, washed with distilled water (100 ml), and dried under vacuum at 75° C. for 2 hours. From the powder of terephthalic acid thus obtained samples are taken for impurity analysis.

The analytic data on the quality of terephthalic acid purified by this method on the catalysts prepared in accordance with the Examples presented hereinabove are listed in Table 6.

As is seen from the Examples and Tables, the proposed invention permits purifying terephthalic acid to a low residual content of p-carboxybenzaldehyde, which makes the proposed method of purifying widely applicable in the chemical industry.

TABLE 1

Main characteristics of some granulated porous carbon materials

| Nos. | Grade | Origin (source) | Appearance | Size, mm | $A_{BET}$[1], $m^2/g$ | $V_{micro}$[2], $cm^3/g$ | $V_{meso}$[3], $cm^3/g$ | $V_\Sigma$[4], $cm^3/g$ | $V_{meso}/V_\Sigma$ | $D_{mean}$[5], Å | κ[6], % |
|---|---|---|---|---|---|---|---|---|---|---|---|
| 1 | AR-B | Coal | Rod- | 4–5 | 438 | 0.192 | 0.027 | 0.219 | 0.12 | 20 | 5 |
| 2 | CG-5 | Coconut carbon | Crushed | 3–6 | 1024 | 0.438 | 0.047 | 0.485 | 0.10 | 19 | 10 |
| 3 | L-2702 | Coal | Rod-like | 4–8 | 1024 | 0.453 | 0.046 | 0.499 | 0.03 | 19 | |
| 4 | FB-4 | Coal | Rod-like | 4–6 | 606 | 0.222 | 0.144 | 0.366 | 0.39 | 24 | |
| 5 | KVU-1 | Hydrocarbons | Granule | 3–5 | 120 | 0.010 | 0.310 | 0.32 | 0.97 | 107 | 40 |
| 6 | Sibunit 1 | Hydrocarbons | Granule | 2–3 | 440 | 0.015 | 0.665 | 0.680 | 0.98 | 62 | 60 |

[1] $A_{BET}(m^2/g)$ is the specific surface area according to BET. The surface area was calculated within the isotherm region where $P/P_0 = 0.05 - 0.20$; the value of the nitrogen molecule area in the filled monomolecular layer was assumed to be equal to $\omega = 0.162$ $nm^2$;
$V_{micro}$ ($cm^3/g$) is the volume of micropores. It was calculated, using comparative method within isotherm regions corresponding to the region between the filling of micropores and the onset of capillary condensation; the value $V_{micro}$ corresponds to the total volume of ultramicro- and supermicropores, that is, to the volume of micropores whose size is smaller than 20 Å;
[3] $V_{meso}$ ($cm^3/g$) = $V_\Sigma - V_{micro}$;
[4] $V_\Sigma(cm^3/g)$ is the volume of pores whose size is smaller than 5000 Å. It is calculated from the adsorption of nitrogen at $P/P_0 = 0.98$;
[5] $D_{mean}$ (Å) is the mean size of pores, calculated as $D_{mean} = 4 \cdot 10^4 \cdot V_\Sigma/A_{BET}$;
[6] κ (%) is the degree of crystallinity, calculated from the integral peak intensity (002); diffractograms were recorded on a HZG-4C diffractometer ($CuK_\alpha$, graphite monochromator).

TABLE 2

Properties of the catalysts

| Example No. | Catalyst composition, percent by weight | Δ[1] Ru | Δ$_{mean}$[2] Ru | Δ Pd | Δ$_{mean}$ Pd |
|---|---|---|---|---|---|
| 1 | 0.5% Pd/Sib.1 | | | 27–75 | 38 |
| 2 | 0.5% Ru/Sib.1 | 18–45 | 32 | | |
| 3 | (0.2% Ru-0.3% Pd)/Sib.1 | 30–91 | 44 | 19–82 | 38 |
| 4 | 0.5% Pd/Sib.1 | | | 58–410 | 302 |
| 5 | 0.5% Ru/Sib.1 | 220–384 | 293 | | |
| 6 | (0.2% Ru-0.3% Pd)/Sib.1 | 90–339 | 240 | 90–298 | 249 |
| 7 | 0.5% Pd/CG-5 | | | 18–75 | 41 |
| 8 | (0.2% Ru-0.3% Pd)/CG-5 | 12–48 | 26 | 9–42 | 22 |
| 10 | (0.3% Ru-0.2% Pd)/Sib.1 | | | 22–79 | 44 |
| 14 | 0.2% Ru/Sib.1 | Fuzzy | ≧475 | | |
| 15 | 0.3% Pd/Sib.1 | | | 261–597 | 371 |
| 16 | 0.3% Pd/Sib.1 | | | 477–1530 | 988 |
| 17 | 0.3% Pd/Sib.1 | | | 17–123 | 46 |
| 18 | 0.3% Pd/0.2% Ru/Sib.1 | 34–716 | 285 | Fuzzy | ≧580 |
| 19 | 0.3% Pd/0.2% Ru/Sib.1 | Fuzzy | ≧766 | 56–183 | 134 |
| 20 | 0.2% Ru/0.3% Pd/Sib.1 | 28–206 | 92 | 14–597 | 211 |
| 21 | 0.2% Ru/0.3% Pd/Sib.1 | 178–505 | 286 | 322–1533 | 739 |
| 22 | 0.2% Ru/0.3% Pd/Sib.1 | 64–673 | 396 | 56–1150 | 200 |
| 23 | 0.2% Ru/0.3% Pd/Sib.1 | 159–430 | 302 | 17–239 | 90 |
| 26 | 0.5% Pd/Sib.1 | | | 51–232 | 121 |
| 30 | 0.5% Pd/AR-B | | | 45–250 | 128 |
| 31 | 0.5% Pd/L-2702 | | | 58–287 | 150 |
| 32 | 0.5% Pd/FB-4 | | | 7–29 | 17 |
| 34 | 0.5% Pd/CG-5 | | | 6–40 | 18 |

[1] Parameter Δ characterizes the thickness of active layer in μm at 1/2 height of the peak of metal distribution in the surface layer of the granule; Δ$_{mean}$ is the arithmetic mean of the parameter Δ.

TABLE 3

Characteristics of TPA purified by the method according to Example 36

| Example No. | Catalyst composition percent by weight | Transmission of alkaline solutions, % 340 nm | Transmission of alkaline solutions, % 400 nm | Content of impurities ppm p-CBA | Content of impurities ppm p-TA |
|---|---|---|---|---|---|
| 1 | 0.5% Pd/Sib.1 | 95.51 | 98.83 | 9 | 3620 |
| 2 | 0.5% Ru/Sib.1 | 84.51 | 96.27 | 25 | 520 |
| 3 | (0.2% Ru-0.3% Pd)/Sib.1 | 93.21 | 98.42 | 12 | 2620 |
| 4 | 0.5% Pd/Sib.1 | 84.57 | 96.86 | 455 | 729 |
| 5 | 0.5% Ru/Sib.1 | 75.78 | 97.43 | 851 | 138 |
| 6 | (0.2% Ru-0.3% Pd)/Sib.1 | 89.31 | 98.47 | 345 | 524 |
| 7 | 0.5% Pd/CG-5 | 66.14 | 81.65 | 16 | 760 |
| 8 | (0.2% Ru-0.3% Pd)/CG-5 | 89.90 | 95.50 | 10 | 3696 |
| 9 | (0.1% Ru-0.4% Pd)/Sib.1 | 95.79 | 99.15 | 9 | 2830 |
| 10 | (0.3% Ru-0.2% Pd)/Sib.1 | 94.18 | 98.56 | 10 | 1640 |
| 11 | (0.1% Ru-0.4% Pd)/Sib.1 | 91.98 | 100.00 | 340 | 602 |
| 12 | (0.3% Ru-0.2% Pd)/Sib.1 | 90.82 | 100.00 | 336 | 394 |
| 13 | 0.2% Ru/Sib.1 | 69.76 | 98.16 | 1265 | 79 |
| 15 | 0.3% Pd/Sib.1 | 77.08 | 95.96 | 842 | 138 |
| 16 | 0.3% Pd/Sib.1 | 78.22 | 96.99 | 772 | 151 |
| 18 | 0.3% Pd/0.2% Ru/Sib.1 | 97.03 | 99.70 | 1402 | 197 |
| 19 | 0.3% Pd/0.2% Ru/Sib.1 | 93.08 | 100.00 | 131 | 914 |
| 20 | 0.2% Pu/0.3% Pd/Sib.1 | 86.52 | 98.67 | 446 | 743 |
| 21 | 0.2% Ru/0.3% Pd/Sib.1 | 77.66 | 97.51 | 973 | 284 |
| 23 | 0.2% Ru/0.3% Pd/Sib.1 | 77.80 | 97.51 | 1303 | 201 |
| 24 | 0.1% Pt/0.5% Pd/Sib.1 | 75.54 | 97.56 | 200 | 689 |
| 25 | 0.1% Rh/0.5% Pd/Sib.1 | 52.57 | 96.30 | 494 | 176 |
| 26 | 0.5% Pd/Sib.1 | 92.88 | 97.17 | 56 | 2251 |
| 27 | 0.5% Pd/Sib.1 | 95.00 | 98.90 | 83 | 3662 |
| 28 | 1% Pd/Sib.1 | 89.50 | 94.23 | 6 | 6048 |
| 29 | 2% Pd/Sib.1 | 100.00 | 100.00 | 15 | 5443 |
| 30 | 0.5% Pd/AR-B | 72.65 | 94.28 | 432 | 235 |
| 31 | 0.5% Pd/L-2702 | 56.28 | 99.00 | 676 | 184 |
| 32 | 0.5% Pd/FB-4 | 59.84 | 92.57 | 412 | 230 |
| 33 | 0.5% Pd/KVU-1 | 94.79 | 94.44 | 6 | 1020 |
| 34 | 0.5% Pd/CG-5 | 98.6 | 100.00 | 6 | 559 |
| 35 | (0.1% Pt-0.4% Pd)/CG-5 | 87.57 | 98.41 | 18 | 1200 |

TABLE 4

Characteristics of TPA purified by the method according to Example 37

| Example No. | Catalyst composition, Percent by weight | Cycle No. | Transmission of alkaline solutions, % 340 NM | Transmission of alkaline solutions, % 400 nm | Content of impurities ppm p-CBA | Content of impurities ppm p-TA |
|---|---|---|---|---|---|---|
| 1 | 0.5% Pd/Sib.1 | 1 | 96.52 | 98.85 | 6 | 7249 |
| | | 2 | 97.18 | 99.52 | 5 | 6955 |
| | | 3 | 94.25 | 98.35 | 5 | 4534 |
| | | 4 | 89.90 | 95.92 | 6 | 2688 |
| | | 5 | 88.55 | 95.63 | 4 | 1058 |
| 2 | 0.5% Ru/Sib.1 | 1 | 89.86 | 97.79 | 24 | 1067 |
| | | 2 | 88.39 | 98.60 | 23 | 546 |
| | | 3 | 84.81 | 100.00 | 25 | 269 |
| | | 4 | 80.46 | 96.16 | 23 | 297 |
| | | 5 | 82.44 | 97.12 | 25 | 199 |
| 3 | (0.2% Ru-0.3% Pd)/Sib.1 | 1 | 95.80 | 99.17 | 11 | 1873 |
| | | 2 | 96.64 | 100.00 | 10 | 1528 |
| | | 3 | 97.50 | 100.00 | 9 | 1218 |
| | | 4 | 89.19 | 96.25 | 14 | 974 |
| | | 5 | 84.46 | 94.30 | 15 | 907 |
| 6 | (0.2% Ru-0.3% Pd)/Sib.1 | 1 | 93.80 | 99.08 | 6 | 1990 |
| | | 2 | 92.06 | 97.08 | 8 | 1033 |
| | | 3 | 90.51 | 97.42 | 53 | 949 |
| | | 4 | 88.76 | 97.47 | 85 | 1117 |
| | | 5 | 82.00 | 97.85 | 206 | 1151 |
| 7 | 0.5% Pd/CG-5 | 1 | 98.11 | 100.00 | 5 | 4402 |
| | | 2 | 97.74 | 100.00 | 7 | 1391 |
| | | 3 | 94.78 | 99.08 | 12 | 748 |
| | | 4 | 91.95 | 99.22 | 52 | 882 |
| 8 | (0.2% Ru-0.3% Pd)/CG-5 | 1 | 99.27 | 100.00 | 9 | 5275 |
| | | 2 | 99.30 | 100.00 | 40 | 1613 |
| | | 3 | 96.53 | 100.00 | 34 | 3142 |
| | | 4 | 91.38 | 98.26 | 60 | 511 |
| | | 5 | 90.91 | 99.46 | 202 | 442 |
| 19 | 0.3% Pd/0.2% Ru/Sib.1 | 1 | 93.84 | 99.18 | 12 | 7200 |
| | | 2 | 90.67 | 97.65 | 88 | 6200 |
| | | 3 | 94.78 | 100.00 | 279 | 756 |

TABLE 4-continued

Characteristics of TPA purified by the method according to Example 37

| Example No. | Catalyst composition, Percent by weight | Cycle No. | Transmission of alkaline solutions, % 340 NM | Transmission of alkaline solutions, % 400 nm | Content of impurities ppm p-CBA | Content of impurities ppm p-TA |
|---|---|---|---|---|---|---|
| | | 4 | 83.80 | 96.18 | 366 | 873 |
| | | 5 | 79.52 | 95.06 | 297 | 672 |
| 20 | 0.2% Ru/0.3% Pd/Sib.1 | 1 | 97.13 | 100.00 | 8 | 1267 |
| | | 2 | 90.87 | 100.00 | 219 | 571 |
| | | 3 | 82.48 | 100.00 | 865 | 549 |
| | | 4 | 76.62 | 100.00 | 1213 | 477 |
| | | 5 | 68.24 | 96.39 | 1312 | 319 |
| 23 | 0.2% Ru/0.3% Pd/Sib.1 | 1 | 96.80 | 100.00 | 255 | 899 |
| | | 2 | 83.89 | 97.13 | 405 | 168 |
| | | 3 | 75.50 | 94.09 | 778 | 124 |
| | | 4 | 70.48 | 93.70 | 814 | 155 |
| | | 5 | 67.61 | 94.70 | 1003 | 286 |
| 26 | 0.5% Pd/Sib.1 | 1 | 97.87 | 100.00 | 10 | 2612 |
| | | 2 | 98.71 | 100.00 | 10 | 2352 |
| | | 3 | 95.33 | 100.00 | 6 | 361 |
| | | 4 | 92.26 | 99.44 | 72 | 470 |
| | | 5 | 86.55 | 97.88 | 198 | 655 |
| 34 | 0.5% Pd/CG-5 | 1 | 94.85 | 96.84 | 8 | |
| | | 2 | 95.41 | 100.00 | 11 | |
| | | 3 | 93.72 | 98.87 | 71 | |
| | | 4 | 91.28 | 97.72 | 360 | |
| | | 5 | 89.16 | 97.24 | 739 | |

TABLE 5

Characteristics of TPA purified by the method according to Example 38 (with the initial p-CBA content of 30,000 ppm)

| Ex. No. | Catalyst composition, Percent by weight | Cycle No. | Transmission of alkaline solutions, % 340 NM | Transmission of alkaline solutions, % 400 nm | Content of p-CBA ppm |
|---|---|---|---|---|---|
| 3 | 0.2% Ru-0.3% Pd)/Sib.1 | 1 | 92.22 | 97.00 | 10 |
| | | 2 | 94.34 | 98.33 | 20 |
| | | 3 | 93.93 | 97.46 | 31 |
| | | 4 | 79.58 | 93.73 | 41 |
| | | 5 | 77.89 | 93.46 | 156 |
| 34 | 0.5% Pd/CG-5 | 1 | 97.95 | 98.54 | 9 |
| | | 2 | 91.15 | 97.67 | 37 |
| | | 3 | 88.29 | 97.68 | 434 |
| | | 4 | 72.85 | 97.52 | 1607 |
| | | 5 | 41.71 | 92.83 | 3447 |

TABLE 6

Characteristics of TPA purified by the method according to Example 39

| Example No. | Catalyst composition, percent by weight | Duration of experiment (t), hr | Weight of catal. ($P_{wt}$), g | $L_w$[1] | Transmission of alkaline solutions, 340 nm | Transmission of alkaline solutions, 400 nm | Content of impurities, ppm p-CBA | Content of impurities, ppm p-TA |
|---|---|---|---|---|---|---|---|---|
| 1 | 0.5% Pd/Sib.1 | 8 | 2.00 | 29.5 | 90.7 | 97.2 | 15 | 460 |
| 3 | 0.2% Ru-0.3% Pd/Sib.1 | 10 | 2.00 | 4.2 | 92.17 | 99.21 | 32 | 1930 |
| 3 | 0.2% Ru-0.3% Pd/Sib.1 | 10 | 2.00 | 18.8 | 83.01 | 91.88 | 80 | 116 |
| 4 | 0.5% Pd/Sib.1 | 10 | 2.00 | 1.2 | | | 55 | 1242 |
| 4 | 0.5% Pd/Sib.1 | 10 | 2.00 | 20.3 | 86.6 | 99.3 | 189 | 10 |
| 7 | 0.5% Pd/CG-5 | 10 | 2.00 | 22.4 | 88.75 | 97.19 | 164 | 39 |
| 8 | 0.2% Ru-0.3% Pd/CG-5 | 10 | 2.00 | 17.3 | 92.13 | 99.27 | 100 | 152 |
| 33 | 0.5% Pd/KBU-1 | 10 | 2.00 | 20.1 | 87.81 | 98.46 | 80 | 162 |
| 34 | 0.5% Pd/CG-5 | 10 | 2.00 | 20.2 | 89.7 | 95.3 | 15 | 162 |

[1] Bulk load on the catalyst $L_w = W_{TPA}/(P_{wt} \cdot t)$, where $W_{TPA}$ is the volume of TPA solution passed through catalyst layer during the time t.

What is claimed is:

1. A catalyst composition for the purification of terephthalic acid from p-arboxybenzaldehyde comprising crystallites of catalytically active palladium or palladium and at least one metal of Group VIII of the Periodic Table of Elements, applied to the surface of a carbon material, wherein a mesoporous graphite-like material with the average mesopore size in the range of from 40 to 400 Å, the proportion of the mesopores in the total pore volume of at least 0.5, and the degree of graphite-similarity of at least 20% is used as the carbon material, in which metal crystallites are distributed in the volume of the carbon material granules in such a manner that the distribution peaks of these crystallites should be at a distance from the outer surface of the granule corresponding to 1–30% of its radius.

2. The catalyst composition of claim 1, wherein it comprises crystallites of rhodium and palladium.

3. The catalyst composition of claim 1, wherein it comprises crystallites of palladium and ruthenium.

4. The catalyst composition of claim 1, wherein it comprises crystallites of palladium and platinum.

5. The catalyst composition of claim 1, wherein the total content of metals therein varies within the range of from 0.1 to 3.0 percent by weight.

6. The catalyst composition of claim 1, wherein the weight ratio of palladium to other metals varies within the range of from 0.1 to 10.0.

7. A method of preparing a catalyst composition for the purification of terephthalic acid from p-carboxybenzaldehyde, claimed in claim 1, comprising in applying catalytically active palladium or palladium and at least one of Group VIII metals to the surface of granules of a carbon carrier, said granules being contacted with an aqueous solution of palladium salts or palladium salts and salts of at least one of Group VIII metals to produce a "metal salt—porous carbon" precursor, wherein the precursor is dried and treated with a reducing agent in an amount sufficient for reducing the surface metal salts to the metal crystallites, characterized in that a mesoporous graphite-like material with the average mesopore size in the range of from 40 to 400 Å, the proportion of the mesopores in the total pore volume of at least 0.5, and the degree of graphite-similarity of at least 20% is used as the carbon material to produce a metallic or bimetallic catalyst.

8. The method of claim 7, wherein said catalyst composition is prepared, using one of the following metal precursors:

$H_2PdCl_4$ or $Pd(NO_3)_2$;

$H_2PdCl_4$ and $RuOHCl_3$ or $RuNO(NO_3)_3$;

$Pd(NO_3)_2$ and $RuOHCl_3$ or $RuNO(NO_3)_3$.

9. The method of claim 7, wherein said catalyst composition is prepared, using nitric acid solutions of palladium and/or ruthenium salts with the concentration of free nitric acid ranging from 37 to 170 g/l.

10. The method of claim 7, wherein bimetallic catalysts are prepared by combined application of metal precursors.

11. The method of claim 7, wherein bimetallic catalysts are prepared by successive application of metal precursors.

12. A method for the purification of crude terephthalic acid comprising p-carboxybenzaldehyde wherein said method comprises contacting an aqueous solution of the crude terephthalic acid with a catalyst according to claim 1 at elevated temperature and in the presence of hydrogen and thereafter cooling the hydrogenated aqueous solution to effect separation of the resulting purified terephthalic from said solution by crystallization.

13. The method of claim 12, wherein the catalyst composition comprises crystallites of palladium and rhodium.

14. The method of claim 12, wherein the catalyst composition comprises crystallites of palladium and ruthenium.

15. The method of claim 12, wherein the catalyst composition comprises crystallites of palladium and platinum.

16. The method of claim 12, wherein the total content of metals in the catalyst composition varies within the range of from 0.1 to 3.0 percent by weight.

17. The method of claim 12, wherein the weight ratio of palladium to other metals in the catalyst composition varies within the range of 0.1 to 10.0.

18. The method of claim 12, wherein the concentration of p-carboxybenzaldehyde in terephthalic acid to be purified varies from 1000 to 30000 ppm.

* * * * *